United States Patent [19]

Abrahamson et al.

[11] Patent Number: 5,382,238

[45] Date of Patent: Jan. 17, 1995

[54] CATHETER STIFFENERS

[75] Inventors: Timothy A. Abrahamson, Seattle; Richard K. Sommercorn, Renton, both of Wash.

[73] Assignee: Quinton Instrument Company, Bothell, Wash.

[21] Appl. No.: 65,081

[22] Filed: May 20, 1993

[51] Int. Cl.⁶ .................... A61M 5/172; A61M 25/00
[52] U.S. Cl. ..................... 604/170; 604/282; 128/657
[58] Field of Search ............ 604/158, 164, 170, 204, 604/280, 282; 128/657, 772

[56] References Cited

U.S. PATENT DOCUMENTS

| | | | |
|---|---|---|---|
| 272,651 | 2/1884 | Mahurkar | D24/54 |
| 958,854 | 5/1910 | Bunn | |
| 1,920,006 | 7/1933 | Dozier | |
| 2,393,003 | 1/1946 | Smith | |
| 3,811,449 | 5/1974 | Gravlee et al. | |
| 3,817,809 | 6/1974 | Dereniuk | 156/296 |
| 3,867,945 | 2/1975 | Long | |
| 4,037,599 | 7/1977 | Raulerson | |
| 4,327,722 | 5/1982 | Groshong et al. | |
| 4,345,606 | 8/1982 | Littleford | 128/784 |
| 4,369,790 | 1/1983 | McCarthy | 604/280 |
| 4,402,684 | 9/1983 | Jessup | 604/264 |
| 4,405,314 | 9/1983 | Cope | 604/51 |
| 4,431,426 | 2/1984 | Groshong et al. | |
| 4,504,268 | 3/1985 | Herlitze | 604/170 |
| 4,543,087 | 9/1985 | Sommercorn et al. | 604/43 |
| 4,549,879 | 10/1985 | Groshong et al. | |
| 4,559,046 | 12/1985 | Groshong et al. | |
| 4,571,239 | 2/1986 | Heyman | 604/54 |
| 4,636,200 | 1/1987 | Vaillancourt | 604/170 |
| 4,659,328 | 4/1987 | Potter et al. | 604/170 |
| 4,682,978 | 7/1987 | Martin | 604/43 |
| 4,698,056 | 10/1987 | Ciannella | 604/164 |
| 4,713,049 | 12/1987 | Carter | 604/8 |
| 4,773,416 | 9/1988 | Houralane | 128/303 R |
| 4,798,193 | 1/1989 | Giesy et al. | 128/7 |
| 4,804,365 | 2/1989 | Litzie et al. | 604/4 |
| 4,824,435 | 4/1989 | Giesy et al. | 604/49 |
| 4,826,485 | 5/1989 | Johnson | 604/170 |
| 4,834,709 | 5/1989 | Banning et al. | 604/170 |
| 4,844,092 | 7/1989 | Rydell et al. | 128/772 |
| 4,863,430 | 9/1989 | Klyre et al. | 604/164 |
| 4,871,356 | 10/1989 | Haindl et al. | 604/247 |
| 4,947,864 | 8/1990 | Shockey et al. | 128/772 |
| 4,969,875 | 11/1990 | Ichikawa | 604/164 |
| 4,983,170 | 1/1991 | Etheredge, III et al. | 604/270 |
| 5,030,227 | 7/1991 | Rosenbluth et al. | 606/192 |
| 5,053,004 | 10/1991 | Markel et al. | 604/43 |
| 5,092,847 | 3/1992 | Pozzo | 604/170 |
| 5,106,377 | 4/1992 | Martin | 604/164 |
| 5,116,309 | 5/1992 | Coll | 604/8 |
| 5,183,470 | 2/1993 | Wettermann | 604/281 |
| 5,221,255 | 6/1993 | Mahurkar et al. | 604/43 |
| 5,263,928 | 11/1993 | Trauthen et al. | 604/53 |

Primary Examiner—John D. Yasko
Assistant Examiner—Adam J. Cermak
Attorney, Agent, or Firm—Andrew J. Beck; Montgomery W. Smith; Richard D. Allison

[57] ABSTRACT

A catheter assembly including a wire stiffener or a dilator and modified wire stiffener which are used in combination to assist in the insertion of a relatively soft catheter into the patient wherein the wire stiffener temporarily stiffens the catheter and the modified wire stiffener temporarily stiffens the dilator for insertion of the combined wire stiffener and dilator into the catheter. The catheter preferably includes one or more lumens therein and includes an end opening and one or more side openings thereon.

16 Claims, 6 Drawing Sheets

CATHETER STIFFENERS

FIELD OF THE INVENTION

The present invention relates to an improved catheter dilator stiffener for use in medical applications such as hemodialysis where it is desirable to use catheters having sufficient softness and flexibility to remain inserted in the patient for extended periods of time.

BACKGROUND OF THE INVENTION

Dilators have been used by the medical community for many years. Dilators are commonly used by physicians to enlarge an incision prior to the introduction of a larger catheter or to temporarily stiffen a catheter during insertion.

A preferred non-surgical method for inserting a catheter involves the use of the Seldinger technique which includes an access needle that is inserted into the patient's vein. A guidewire is then inserted through the needle and into the vein. The needle is then removed and a dilator is inserted over the guidewire. The dilator is inserted a short distance into the tissue to dilate the incision and the dilator is then removed and discarded. The catheter is then inserted into the vein in the desired location.

Many long-term catheters are made of either a semi-rigid material such as a polyurethane or a soft material such as a soft urethane or silicone rubber. Many polyurethane catheters are sufficiently rigid to be introduced into a patient's vein percutaneously without surgery. However, one of the difficulties with many rigid polyurethane catheters is that they may be incompatible with the human body when left in place for long periods of time. The silicone catheters may be left in place for longer periods of time than many of the polyurethane catheters without traumatic problems in most patients. However, one of the difficulties with silicone catheters is that the initial insertion of such catheters usually requires surgical intervention because the soft, pliable, elastic properties of the silicone which contribute to its compatibility with the human body are the same properties that make it difficult or impossible to insert the silicone catheter percutaneously into the vein of the patient.

Another insertion difficulty arises during the insertion of the dilator into the soft catheter and the subsequent insertion of the dilator into the incision. If the dilator is too soft, the user may have difficulty inserting the dilator into the catheter due to the frictional resistance encountered while inserting the dilator into the catheter. If the dilator is too rigid, the user may injure the blood vessel of the patient as the dilator and catheter are inserted into the incision. In the past, prior devices have attempted to overcome the problem of inserting a dilator into the catheter by providing a dilator having a diameter which is significantly less than the diameter of the lumen of the catheter. In addition to the reduced external diameter of the dilator, the inner diameter of the opening on the distal end of the catheter was also reduced so that pressure on the dilator when it is inserted into the catheter will cause the dilator to contact the distal end of the catheter and thereby push the catheter into the incision. If the contact between the dilator and distal end of the catheter were not present, the insertion force by the dilator may cause the catheter body to expand against the incision and slide along the dilator, thereby preventing the catheter from sliding through the incision. Additionally, if the transition between the outer diameter of the dilator and the distal end of the catheter were not a smooth transition, there is an increased likelihood that the tissue will be torn rather than dilated by the catheter.

In one currently available hemodialysis catheter combination sold by Medical Components, Inc., of Harleysville, Pa., U.S.A., a silicone double lumen catheter is used with an inner Teflon ® stylet. The Teflon ® stylet is used to increase the stiffness of the catheter as the combination is inserted into the patient. The stylet is then removed from the catheter once the catheter is inserted into the patient.

A further problem created by the use of the reduced diameter opening on the distal end on the catheter is that the reduced diameter opening restricts the amount of fluid which may flow through the lumen of the catheter. This may create a lower flow area at the transition between the lumen of the catheter and the distal opening if further openings are present in the lumen. This may result in an increased likelihood of clotting in this flow transition area because the flow may be diverted to the side openings in the lumen rather than through the distal opening.

In the preferred form of the present invention a wire stiffener is provided. The wire stiffener provides many of the advantages of a conventional dilator while eliminating the disadvantages of a conventional dilator. The wire stiffener of the preferred embodiment is inserted into the catheter prior to the insertion of the wire stiffener and catheter combination over the guidewire and into the incision.

An alternate embodiment of the present invention overcomes the foregoing disadvantages of a conventional dilator by providing a stiffening wire which is initially inserted into the dilator to assist in the placement of the dilator into the catheter.

SUMMARY OF THE INVENTION

It is a primary object of this invention to provide an improved catheter insertion assembly wherein the catheter may be made of silicone or other relatively soft material which is unlikely to be rejected by the body, and thus can be used for relatively long-term applications and yet may be inserted into a patient percutaneously.

It is yet another object of the present invention to provide a wire stiffener which includes an area of increased flexibility to accommodate the flexing of the extension members on the proximal end of the catheter.

It is a further object of the present invention to provide a catheter and wire stiffener or modified dilator assembly which may each include a lubricous coating thereon to reduce the friction therebetween.

It is yet another object of the present invention to provide a wire stiffener which has sufficient stiffness to facilitate the insertion of the combined wire stiffener and catheter into the patient.

The present invention may generally include a catheter assembly having:
- an elongate wire stiffener having distal and proximal end portions thereon and wherein said distal end portion includes a hub member thereon;
- an elongate dilator having distal and proximal end portions and a lumen extending therethrough wherein said lumen is sized to receive said wire stiffener substantially therein, said proximal end portion including a hub member thereon which is formed to releasably engage said hub member of said stiffening wire; and an elongate catheter having distal and proximal end portions and at least one lumen extending therethrough wherein said lumen is sized to receive said dilator substantially therein, said proximal end portion including a hub member thereon which is formed to releasably engage said hub member of said dilator thereon; and may also include an elongate catheter having distal and proximal end portions and at least first and second lumens formed by a septum extending along a longitudinally extending axis thereof and wherein said first lumen extends between said proximal end portion and an opening on said distal end portion and is sized to receive said dilator substantially therein and said second lumen extends between said proximal end portion of said catheter and a further opening in said catheter.

Additionally, the present invention may generally include a catheter assembly having:

an elongate catheter member having distal and proximal end portions and a lumen extending therebetween; and an elongate stiffening member having distal and proximal end portions with one or more wire members having a first diameter extending therebetween, said distal end portion forming a distal tip having a diameter which is larger than said diameter of said one or more wire members and which is sized to be received through the lumen of a catheter and may also include the distal tip having a lumen extending therethrough, and said lumen is sized to receive a guidewire therein; and/or a proximal end portion of said catheter member which includes a hub member thereon, and said hub member of said catheter member is sized to receive said hub member located on said proximal end portion of said stiffener member releasably connected thereon.

In accordance with the preferred form of the present invention, the foregoing objectives are realized by providing an assembly which includes a catheter comprising an elongated cylindrical tube made of a relatively soft elastic material, such as silicone, and preferably having a lumen therein having an inner diameter which is substantially equal to the inner diameter of an opening at the distal end of the catheter. The assembly also preferably includes an elongate and semi-rigid wire stiffener which is sized to be received in the catheter to temporarily stiffen the catheter during the insertion of the combination into the patient.

In a preferred embodiment, the distal end of the wire stiffener may be coated with a nonreactive hydrophilic coating and used in a multi-lumen hemodialysis catheter of the type generally shown in U.S. Pat. Nos. 4,134,402; 4,568,329; 4,583,968 and 4,962,141. Although these patents disclose a catheter having "D" shaped lumens, the wire stiffener may be used with catheters having one or more lumens with nearly any shape. In this preferred embodiment, the circular cross section of the lumen of the catheter tip is generally the same cross-sectional area as the "D" shape lumen of the catheter. In a further preferred embodiment of the present invention, the lumen which communicates with the catheter tip does not include side holes therein.

In a further preferred embodiment of the present invention, the wire stiffener is a separately supplied member which may be used with a variety of catheters and includes a distal end which is shaped similar to the shape of the conventional dilator and a proximal end shaped like a luer connector. The distal end and the proximal end in this embodiment are interconnected by an elongate wire stiffener. The proximal portion of the wire stiffener preferably includes an area of increased flexibility thereon to complement the flexibility of the proximal portion of the catheter such as in an extension member as described below. Alternately, the wire stiffener may include one or more areas of increased flexibility thereon which correspond to a portion of a catheter which is curved after insertion into the body of the patient such as in various diagnostic or other catheters.

This invention also provides a method of introducing a catheter, such as a dual lumen hemodialysis catheter into the subclavian or jugular vein of the patient for relatively long-term use or into the femoral vein of the patient for shorter term use. The method includes the initial insertion of a wire stiffener into the catheter and then the subsequent insertion of the catheter and wire stiffener combination into the patient. Once the combination is inserted into the patient, the wire stiffener is removed from the catheter and the catheter is used in the patient in a conventional manner as described more fully below.

In a further embodiment of this invention, a modified dilator assembly is disclosed that includes a wire stiffener which may operate as a pull string or a thin flexible wire member. The use of the pull string allows the user to thread the pull string through a dilator and then use the pull string to push the dilator through the catheter. With this embodiment, the user may then withdraw the pull string from the proximal end of the dilator prior to inserting the catheter and dilator over the guidewire and into the patient thereby enabling the convenient insertion of the dilator into the catheter prior to use of the catheter.

In a further embodiment of the present invention the catheter includes two or more lumens extending therethrough and one of the lumens preferably includes only a single opening in the distal end of the catheter tip.

An advantage of the present invention is that it allows for the use of a semi-rigid dilator with a soft catheter while enabling the user to easily insert the dilator into the catheter.

Another advantage of the present invention is that it is relatively simple to use and provides a reliable means for inserting a modified dilator assembly or wire stiffener into a catheter and the insertion of the catheter combination into the blood vessel of a patient.

A further advantage of the present invention is that it may be used with a variety of catheters to increase the ease of insertion of relatively soft catheters into the body of a patient.

A further advantage of the present invention is that the wire stiffener preferably includes one or more areas of increased flexibility thereon.

DESCRIPTION OF THE PREFERRED EMBODIMENTS

As shown in FIGS. 1-8, the catheter assembly 10 of the preferred form of the present invention generally includes an elongate wire stiffener which is insertable into an elongate and flexible catheter 14. The catheter 14 preferably includes one or more lumens therein which may be generally of the type shown in FIG. 2. As used herein the term "distal" is intended to refer to the end or portion of a member which is nearest the patient while the term "proximal" is intended to refer to the end or portion of a member which is normally oriented or positioned away from the patient.

Figure 1:
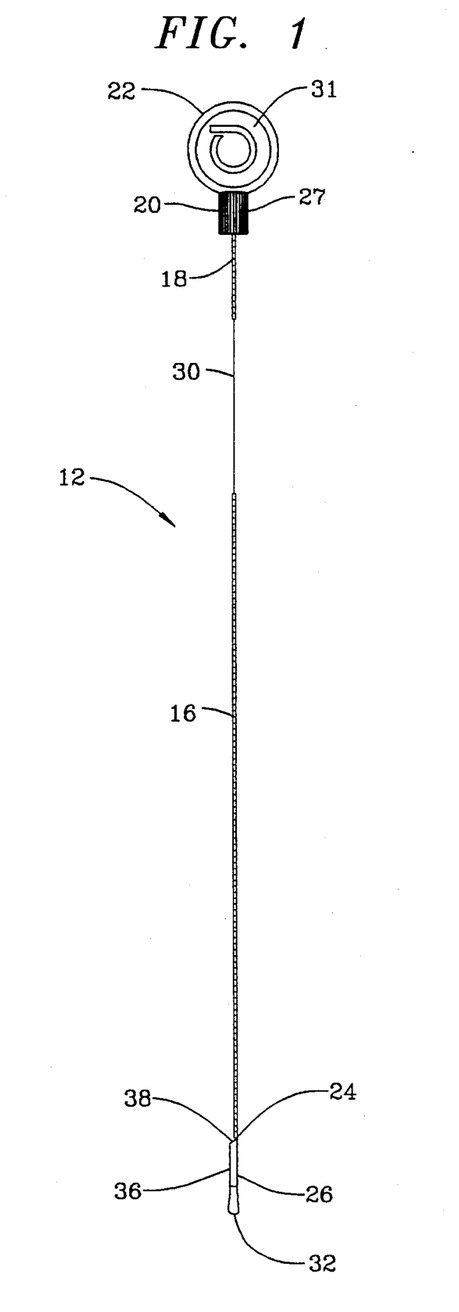
FIG. 1 is an elevated side view of the wire stiffener in the preferred form of the present invention.
Figure 4:
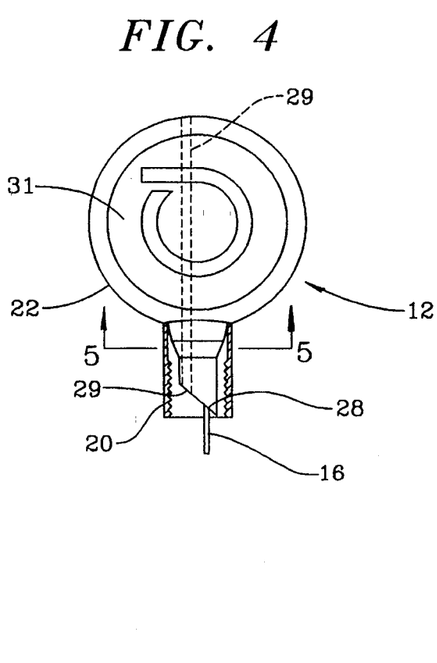
FIG. 4 is an enlarged side view partially in cross section showing the proximal portion of the wire stiffener of FIG. 1 with the threaded cap member in cross section.

The wire stiffener 12 preferably includes an elongate length of wire 16. Alternately, the wire 16 may be formed of plastic or multiple strands of twisted, braided or otherwise oriented strands of wire or even a plurality of separate and spaced apart strands of wire. The wire stiffener 12 consists of a proximal end portion 18 having a threaded cap member 20 and handle member 22 thereon and a distal end portion 24 which includes a distal tip 26 thereon. The distal tip 26 is preferably molded or otherwise fixedly attached to the distal end of the wire 16. As shown in FIG. 1, the threaded cap member 20 on the proximal end portion 18 of the wire stiffener 12 preferably encircles a portion of the handle member 22 and includes a plurality of longitudinal ribs 27 on the exterior surface thereof. The interior surface of the threaded cap member 20 is preferably threaded to create a luer lock type of connection with the proximal portion of the catheter 14 as described more fully below. Alternately, the threaded cap member 20 may be snap fit or otherwise releasably attached to the proximal portion of the catheter 14. The wire 16 is preferably molded or otherwise fixedly attached to the interior of the handle member 22. A tapered or otherwise shaped guidewire alignment surface 28 is also located inwardly of the distal side of the handle member 22 to capture and guide a guidewire into the passageway 29 which extends longitudinally through the threaded cap member 20 and handle member 22 as described more fully below. As shown in FIG. 4, the alignment surface 28 preferably includes a surface of approximately 45 degrees to receive the guidewire in the passageway 29 while the wire 16 of the wire stiffener 14 is offset therefrom.

Figure 5:
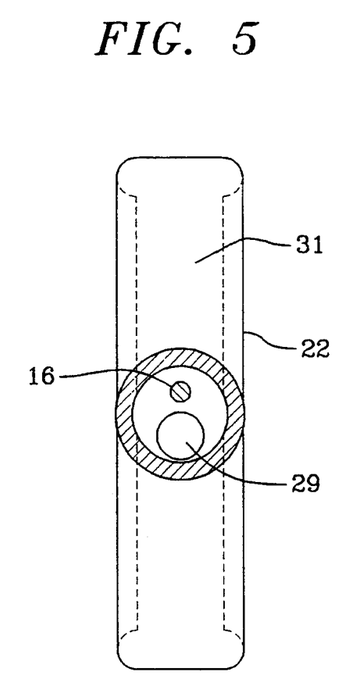
FIG. 5 is an enlarged cross-sectional view showing the proximal portion of the wire stiffener of FIG. 1 taken generally along lines 5—5 of FIG. 4.
Figure 8:
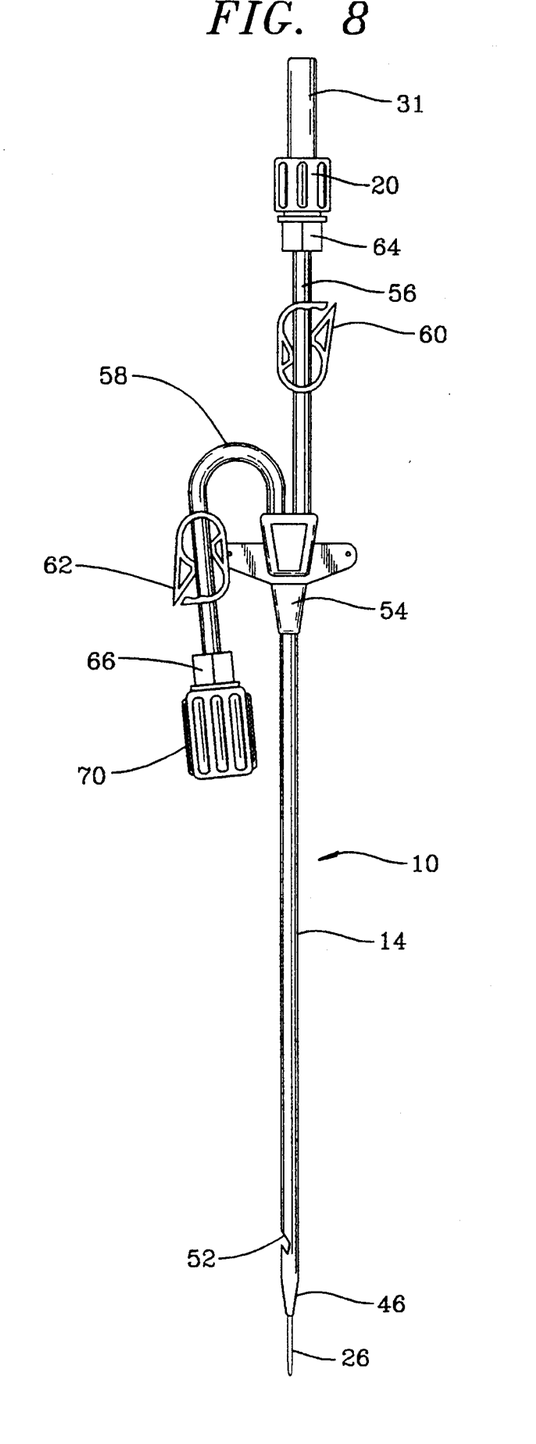
FIG. 8 is an elevated side view of an alternate form of the present invention with the wire stiffener positioned in a dual lumen hemodialysis catheter with the extension tube straightened.

As shown in FIGS. 1, 5 and 8, the finger member 31 of the handle member 22 preferably has a pair of flat side surfaces and is circularly shaped when viewed from the side to provide the user with a member which is easy to grasp during the removal of the wire stiffener 12 from the catheter 14 as described below. Additionally, the threaded cap member 20 is connected to the handle member 22 between the finger member 31 and the alignment surface 28 as shown in FIG. 4. The finger member 31 also includes the passageway 29 extending therethrough to allow at least a portion of the guidewire to extend proximally thereof as described below.

The wire 16 of the wire stiffener 12 is an elongate member which has sufficient stiffness to assist in the insertion of the catheter assembly 10 into the patient. As described above, the wire 16 includes the distal tip 26 fixedly connected to the distal end thereof and the handle member 22 fixedly connected to the proximal end thereof. An area of increased flexibility 30 is preferably located along a proximal portion of the wire 16 as shown in FIG. 1. In the preferred form of the present invention, the flexible area 30 is formed by grinding down or otherwise reducing the diameter of the proximal portion of the wire 16. This flexible area 30 consists of a reduced diameter or reduced thickness portion of the wire 16 to form an area on the wire stiffener 12 which is more easily bent or flexed than the rest of the wire 16 without compromising the required tensile strength of the wire stiffener 12. The location of the flexible area 30 on the wire 16 is dependent on a number of considerations, including the intended use of the catheter the presence of pre-curved or bent extension tubing on the catheter 14, the length of the catheter 14 and the type of packaging used for the catheter assembly 10. Additionally the thickness of the flexible area 30 or, less preferably, the overall stiffness of the wire 16 may be increased or decreased depending on the amount of flexibility or stiffness desired for the optimal insertion of a particular catheter 14 into the patient as described below. In the preferred form of the wire stiffener 12, the flexible area 30 is preferably located along the proximal portion of the wire 16 to correspond with the location of the extension tubing in the catheter 14. Alternately, it is anticipated that the flexible area 30 could be located along the distal portion of the wire 16 to correspond to the curve of a preformed tip of the catheter or to correspond to any other area on the catheter which is curved or bent during insertion. An example of this is shown generally in FIG. 9.

Figure 3:
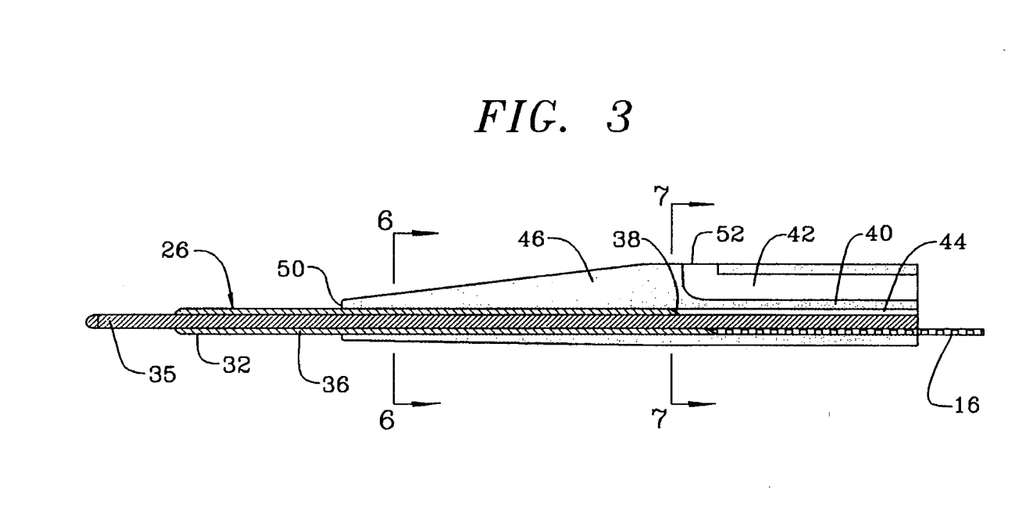
FIG. 3 is an enlarged longitudinal cross-sectional view showing the distal portion of the catheter assembly and wire stiffener of FIG. 2.

As shown best in FIG. 3, the distal tip 26 on the distal end of the wire 16 preferably includes three sections thereon, each having slightly different shapes and diameters. The distal section 32 of the distal tip 26 preferably includes a slight radius thereon. Alternately, the distal section 32 of the distal tip 26 may be tapered at an angle of between about 5 to 15 degrees from the longitudinal axis of the wire stiffener 12 to form a generally conically shaped section. The distal section 32 functions as a transition area between the guidewire and the distal portion of the catheter 14 to form an area of gradually increasing diameter of the catheter assembly 10 to facilitate the insertion of the catheter assembly 10 into the patient. As shown in FIG. 3, the distal tip 26 of the wire stiffener 12 also includes a passageway 34 which extends lengthwise through the distal tip 26. The inner diameter of the passageway 34 is sized to generally correspond to the outer diameter of the guidewire 35.

The middle section 36 of the distal tip 26 is located proximally of the distal section 32 and is preferably cylindrically shaped with an outer diameter which corresponds generally to the preferably circular inner diameter of the lumen of the tip of the catheter 14 as described more fully below. The passageway 34 extends longitudinally through the middle section 36 and allows the smooth passage of the guidewire therethrough. The proximal section 38 of the distal tip 26 forms the transition between the distal tip 26 and the wire 16. The proximal section 38 is preferably tapered slightly and includes the proximal opening off the passageway 34 thereon to allow the guidewire 35 to pass proximally from the interior of the distal tip 26 to a location along the wire 16. The proximal section 38 generally conforms to the shape of the transition area in the catheter 14 where the lumen changes from a generally D-shaped cross section to a circular cross section.

The preferred form of a catheter 14 which is suitable for use with the present invention is shown generally in U.S. Pat. No. 4,583,968 granted to Mahurkar on Apr. 22, 1986. The catheter 14 is preferably a relatively soft catheter formed at least partially of a material such as silicone or a soft urethane. The preferred catheter 14 includes a flat, longitudinal septum 40 which divides the interior of the catheter 14 into two generally parallel lumens 42 and 44, each having a generally preferred D-shaped cross section. Alternately, the catheter 14 may include one or more lumens having a variety of cross-sectional shapes such as a coaxial lumen orientation without adversely affecting the performance of the wire stiffener 12. When the present invention is used with hemodialysis catheters the catheter 14 is aligned with the flow of blood in the vein of the patient. Lumen 42 is a blood-intake or arterial lumen and lumen 44 is a blood-return or venous lumen when the stiffener wire 12 is removed from the catheter 14.

Figure 6:
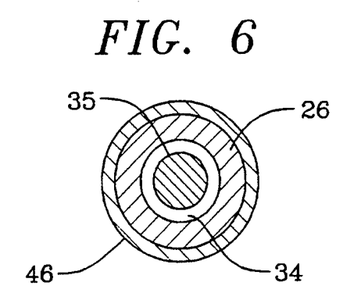
FIG. 6 is a cross-sectional view taken generally along the distal portion of the catheter assembly and wire stiffener of FIG. 2 taken generally along lines 6—6 of FIG. 3.
Figure 7:
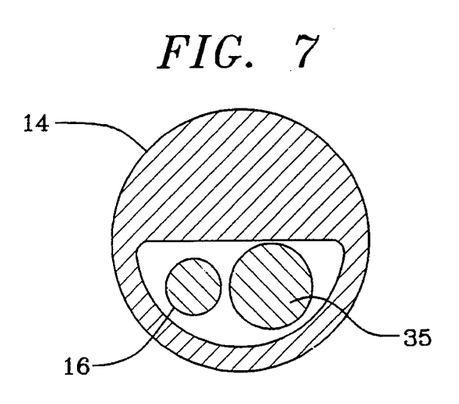
FIG. 7 is a cross-sectional view taken generally along the distal portion of the catheter assembly and wire stiffener of FIG. 2 taken generally along lines 7—7 of FIG. 3 and showing a guidewire inserted therein.

The distal portion of the catheter 14 is preferably formed as a molded conical catheter tip 46 which has a tapered exterior surface to gradually reduce the outer diameter of the distal end portion of the catheter 14 as shown in FIG. 4. The blood-return lumen 44 extends longitudinally from an extension tube on the proximal portion of the catheter 14 through the catheter tip 46. As shown in FIGS. 3 and 6, the blood-return lumen 44 preferably opens at the center of the distal end of the catheter tip 46 as opening 50. Within the catheter tip 46, the diameter of the blood-return lumen 44 of the catheter 14 preferably changes from the D-shaped lumen 44 in the body of the catheter 14 to a circular cross-sectional shape in the catheter tip 46 while preferably maintaining the same general cross-sectional area for each portion of the blood-return lumen 44.

Figure 2:
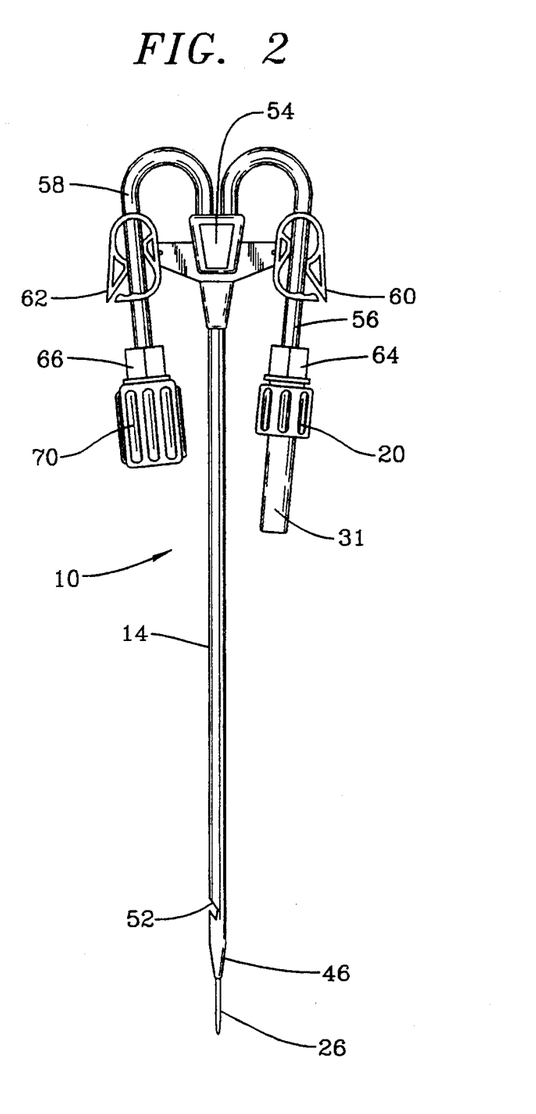
FIG. 2 is an elevated side view of the preferred form of the present invention with the wire stiffener positioned in a dual lumen hemodialysis catheter with the extension members in a pre-curved orientation prior to use of the preferred form of the present invention.

In order to provide longitudinal spacing between the distal openings of the two lumens, 42 and 44, the blood-intake lumen 42 is terminated at a side opening 52 in the sidewall of the catheter 14. FIG. 2 shows the preferred location of the opening 52 on the sidewall of the catheter 14. The opening 52 is preferably either punched, molded, laser or otherwise cut into the sidewall of the catheter 14.

At the proximal end of the catheter 14, the two D-shaped lumens, 42 and 44, open into a Y-shaped connector or hub 54. As shown in FIG. 2, the hub 54 includes a pair of tubular pre-curved extension members, 56 and 58, extending therefrom. Each extension member 56 and 58 includes a clamp member 60 and 62 thereon which serve as on-off valves for controlling the flow of blood between the catheter 14 and a dialysis unit (not shown). The proximal ends of the extension members 56 and 58 include luer connectors 64 and 66 thereon which are initially protected by removable injection caps 70. The injection caps 70 are threadedly received on each of the luer connectors 64 and 66 and include needle pierceable diaphragms thereon. The luer connectors 64 and 66 serve as connectors for connecting the extension members 56 and 58 to various tubes leading to the dialysis unit. The luer connector 64 also receives the threaded cap member 20 of the wire stiffener 12 thereon as shown in FIG. 2 and described more fully below.

When the threaded cap member 20 of the wire stiffener 12 is removably attached to the luer connector 64 on the extension member 56, the length of the wire 16 is such that the distal section 32 of the distal tip 26 extends beyond the catheter tip 46 of the catheter 14. The middle section 36 of the distal tip 26 is received within the catheter tip 46 such that the transition between the distal section 32 and the middle section 36 of the distal tip 26 is positioned at opening 50 on the distal end of the catheter tip 46, and the proximal section 38 is positioned at the transition between the D-shape and circular shape of the blood-return lumen 44. The flexible area 30 of the wire 16 is preferably positioned along the wire 16 so that when the distal tip 26 is properly positioned in the catheter tip 46, the flexible area 30 is positioned within the extension member 56. This positioning of the flexible area 30 of the wire stiffener 12 in the extension member 56 allows the catheter assembly 10 to be shipped and stored with the wire stiffener 12 curved in the pre-curved extension member 56 as shown in FIG. 3 such that the wire stiffener 12 does not straighten the pre-curved extension member 56 prior to use.

The wire stiffener 12 allows the diameter of the opening 50 on the catheter tip 46 to be greater than in prior catheters. In many current prior catheters, the diameter of the opening on the catheter tip is typically approximately equal to the outer diameter of the guidewire. This is because the tissue in the incision or the wall of the blood vessel may snag on the transition between the catheter tip and the guidewire during the insertion of the catheter. The practice of reducing the diameter of the opening on the catheter tip also affects whether or not a side opening is necessary for this lumen to relieve the increased back pressure in the lumen caused by the reduced diameter in the distal tip. In the present embodiment, the middle section 36 of the distal tip 26 fills the transition between the distal hole 50 and the guidewire 35 (FIG. 3) to prevent the tissue or blood vessel wall snag during insertion of the catheter and allows the diameter of the opening 50 on the catheter tip to be sufficiently large so that a further opening in the sidewall of the catheter is not necessary.

The preferred form of the present invention also includes a method of inserting the catheter 14 into an incision in the patient through the use of the wire stiffener 12 and catheter 14 combination as described above. With the preferred form of the present invention, the wire stiffener 12 is supplied to the user installed in the catheter 14. This allows the length of the wire stiffener 12 to be varied according to length of the specific catheter 14. Additionally, the stiffness, tensile strength and the location of the flexible area 30 on the wire stiffener 12 may be varied according to the features of the catheter 14 and the most common insertion techniques used with the particular catheter 14. Alternately, the wire stiffener 12 may be supplied separately or in a kit which may require the user to install the wire stiffener 12 into the catheter 14 prior to the insertion of the catheter 14 into the patient.

The method of inserting the catheter assembly 10 of the present invention includes the conventional insertion steps as described below. An introducer needle (not shown) is used to create the incision or puncture in the patient. The distal end of the introducer needle is advanced into the vein of the patient in the direction of flow of blood through the vein and the proper position of the introducer needle is verified. A guidewire is then inserted into the vein through the introducer needle, and the introducer needle is then removed over the guidewire. Next, if desired, a separate dilator (not shown) may be inserted over the guidewire to pre-dilate the incision prior to the introduction of the combined catheter 14 and wire stiffener.

The catheter 14 and wire stiffener 12 combination are then inserted into the vein of the patient over the guidewire. During this step, the guidewire 35 is initially inserted into the passageway 34 in the distal tip 26 of the wire stiffener 12. The guidewire 35 is then threaded through the passageway 34 of the distal tip 26 and along the length of the wire 16 in the blood-return lumen 44 of the catheter 14. The guidewire 35 is then passed through the hub 54, extension member 56 and luer connector 64 of the catheter 14. The guidewire 35 is threaded into the passageway 29 at the alignment surface 28 and through the threaded cap member 20 and the handle member 22 of the wire stiffener 12 so that the guidewire 35 extends along the wire 16 of the wire stiffener 12 and beyond the proximal end of the catheter assembly 10. Finally, once the catheter 14 is properly positioned in the vein of the patient, the threaded cap member 20 of the wire stiffener 12 is unthreaded or otherwise disconnected from the luer connector 64 of the extension member 56. The wire stiffener 12 and guidewire 35 are then removed from the catheter 14 by grasping the handle member 22 and guidewire 35. The catheter 14 is then readied for conventional use. Alternately, the wire stiffener 12 and guidewire 35 may be removed separately from the catheter 14.

Figure 9:
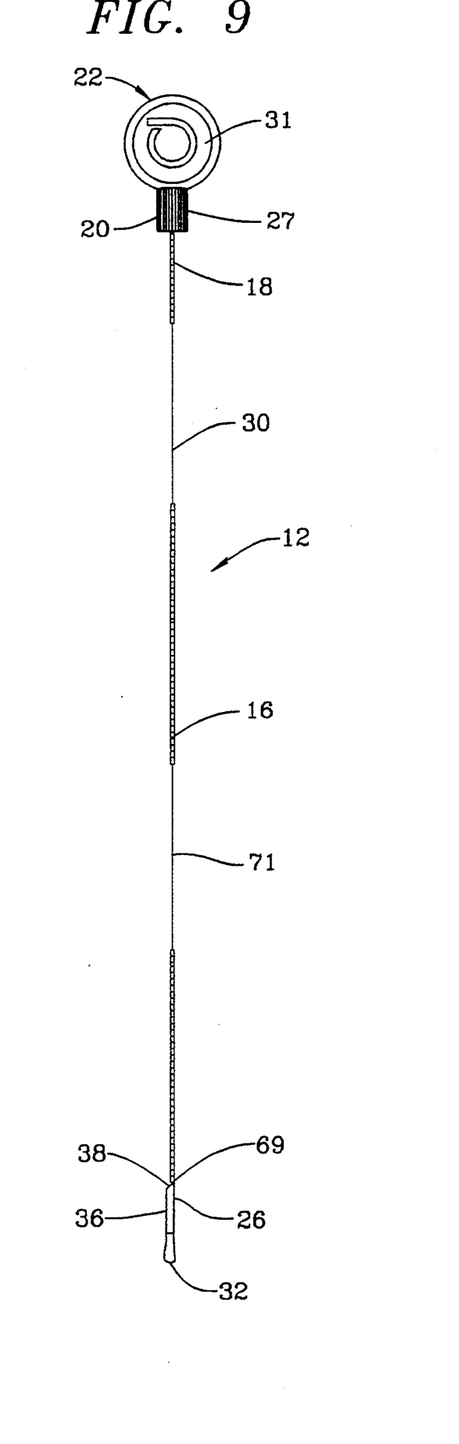
FIG. 9 is an elevated side view of a modified wire stiffener for use with various catheters such as diagnostic catheters wherein it is desirable to have a plurality of areas of increased flexibility along the length of the wire stiffener.
Figure 10A:
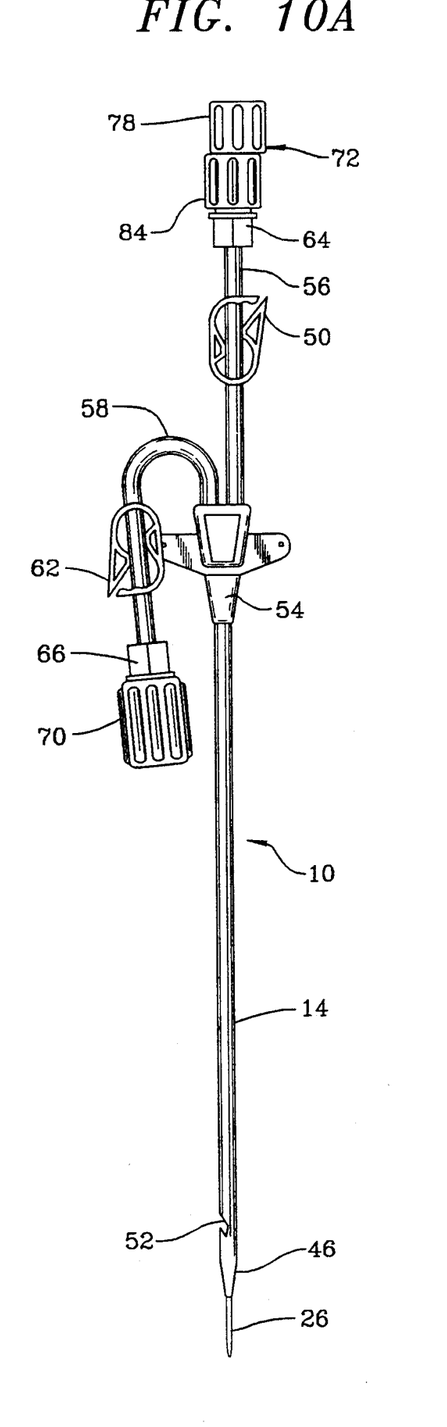
FIGS. 10A and 10B are elevated side views of an alternate embodiment of the present invention showing a modified dilator assembly having a wire stiffener therein.
Figure 10B:
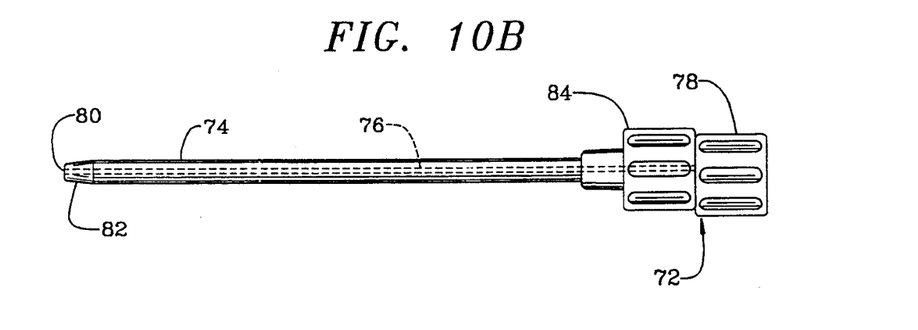
Figure 11A:
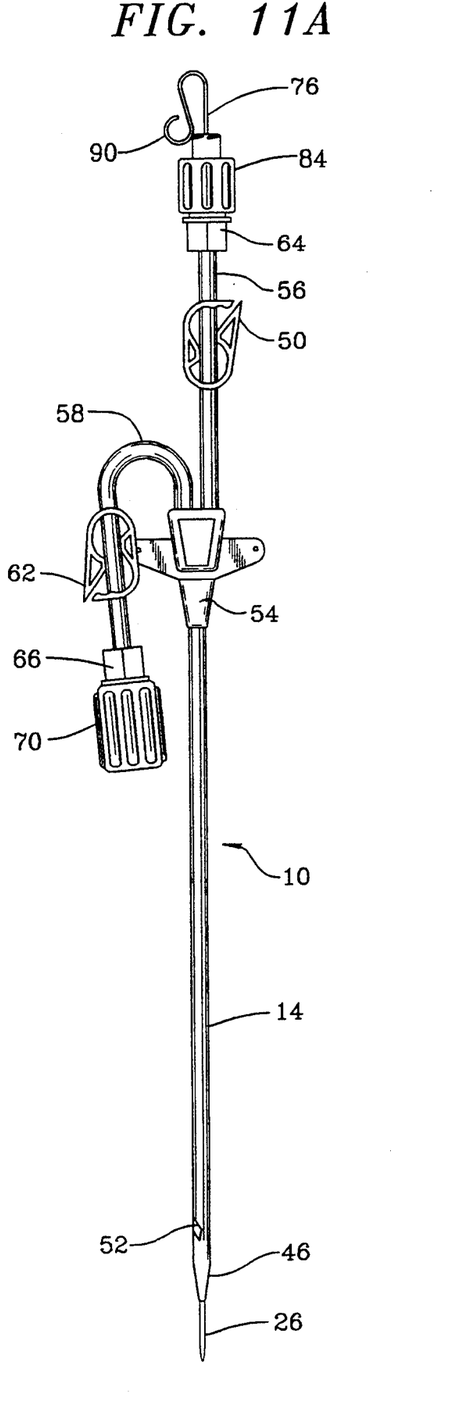
FIGS. 11A and 11B are elevated side views of an of an alternate form of the modified dilator assembly including the wire stiffener and dilator of the embodiment; as generally shown in FIGS. 10A and 10B
Figure 11B:
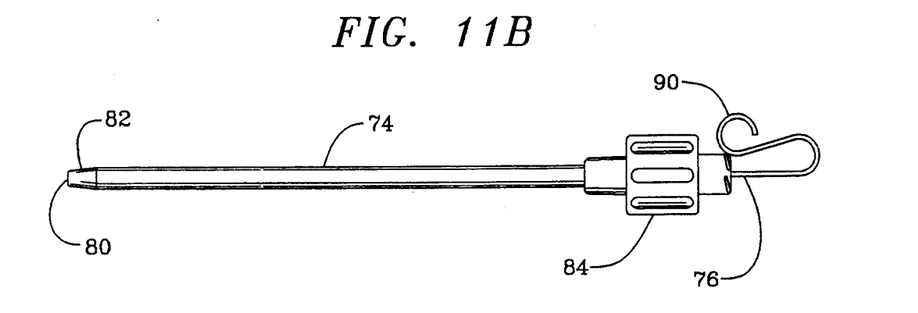

As shown in FIGS. 8 and 9, the wire stiffener 12 may also be modified for use with a variety of other catheters. In the embodiment shown in FIG. 8, the flexible area 30 of the wire stiffener 12 has been removed so that the extension member is straightened prior to use. In the embodiment shown in FIG. 9, the wire stiffener 12 preferably includes a further pair of flexible areas 69 and 71 thereon. The distal flexible area 69 may be used in a catheter 14 which includes a preformed curved distal catheter tip (not shown) such that the wire stiffener 12 does not function to straighten the tip during insertion of the catheter 14 into the patient. The flexible area 71 is preferably positioned along a pre-curved length of the body portion of a catheter 14 so that the wire stiffener 12 does not straighten the body portion of a pre-curved catheter prior to use. It should be understood that although the preferred form of this embodiment would not function to straighten the curvature of the catheter tip, the rigidity of the distal flexible area 69 or the middle flexible area 71 may be varied to partially or completely straighten the catheter tip or body portion of the catheter 14 if this is desirable prior to or during the insertion of the catheter 14 into the patient.

As also shown in FIG. 9, the stiffness of the flexible areas 69 and 71 may be varied such that the middle flexible area 71 may be longer and slightly stiffer than the distal flexible area 69 or the proximal flexible area 30. In this embodiment, the middle flexible area 71 is preferably aligned with a larger and more gradual curve of the catheter than the distal flexible area 69. Therefore, the middle flexible area 71 is preferably longer and has a slightly larger diameter than the distal proximal area 69 in this embodiment.

In the alternate forms of the present invention shown in FIGS. 10A and 10B and FIGS. 11A and 11B, an elongate wire stiffener 72 is used in combination with a dilator 74 to form a modified dilator assembly. The combination of the wire stiffener 72 and the dilator 74 are then insertable into a catheter which preferably includes one or more lumens therein and is generally of the type of catheter described above.

The wire stiffener 72 preferably consists of an elongate and fairly rigid twisted, braided or otherwise oriented length of wire 76. Alternately, a length of rigid plastic or similar material may be used. The wire 76 extends distally from a threaded cap member 78 which is fixedly attached to the proximal end of the wire 76. The threaded cap member 78 preferably includes various threads and tapers on the interior surface thereof to form a luer lock type of connection with the proximal end of the dilator 74 as described more fully below.

The dilator 74 of this embodiment is preferably an elongate tubular member formed of semi-rigid materials such as a urethane or polyethylene. The dilator 74 includes an elongate interior lumen 80 which extends the length thereof and is sized to receive either the wire 76 of the wire stiffener 72, a guidewire (not shown) or fluid therethrough as described below. The exterior surface of the dilator 74 is optionally coated with a hydrophilic lubricant such as a UV cured polyvinylpyrrolidine and has a generally circular cross section. The outer diameter of the dilator 74 is chosen to substantially fill the blood-return lumen 44 of the catheter as described below. The distal end portion 82 of the dilator 74 is preferably tapered to provide a smooth transition between the outer diameter of the guidewire and the catheter. The proximal end of the dilator 74 includes a dilator cap member 84 thereon which includes a proximal surface which is shaped to receive the threaded cap member 78 from the wire stiffener 72 thereon. The distal surface of the threaded cap member 78 is shaped to be received on a luer connector, such as the luer connector 64 described above with respect to the prior embodiments of the present invention and which forms part of the dilator 74 described above.

In the preferred form of the embodiment shown in FIGS. 10 and 11, the wire stiffener 72 preferably has an outer diameter of between about 0.030 and 0.039 and the length of the wire stiffener 72 depends on the usable length of the catheter 14 and extension members, 56 and 58. The inner diameter of the dilator 74 is preferably between about 0.036 and 0.038 for a wire stiffener 72 having an outer diameter of about 0.035 and between about 0.037 and 0.039 for a wire stiffener 72 having an outer diameter of about 0.038. The outer diameter of the dilator 74 is preferably between about 0.066 and 0.079. The inner diameter of the catheter at the catheter tip is preferably between about 0.066 and 0.080. Additionally, the wire stiffener 72 preferably has greater stiffness than the dilator 74, and the dilator 74 has greater stiffness than the catheter 14.

The present embodiment also includes a method of inserting the catheter into an incision in the patient through the use of the wire stiffener 72 and dilator 74 described above. With the preferred form of the present embodiment, the wire stiffener 72 is supplied installed within the dilator 74 such that the threaded cap member 78 is threadedly or otherwise received on the proximal portion of the cap member 84 on the dilator 74, and the wire 76 extends through the lumen 80 of the dilator 74 to provide temporary stiffness to the dilator 74. Alternately, the wire stiffener 72 may be supplied separately from the dilator 74 so that the user will have to initially insert the wire stiffener 72 into the dilator 74. If a hydrophilic coating is used on the exterior surface of the dilator 74, it is then activated by wetting the dilator 74 with a fluid. Next, an injection cap on the luer connector 64 associated with the blood-return lumen is removed, and the wire stiffener 72 and dilator 74 combination are then inserted into the blood-return lumen of the catheter until the distal end portion 82 of the dilator 74 extends beyond the catheter tip and through the opening at the distal end of the catheter. Next, the threaded cap member 78 of the wire stiffener 72 is unthreaded or otherwise disconnected from the dilator cap member 84 of the dilator 74, and the wire stiffener 72 is removed and discarded. The catheter is now ready for use with the dilator 74 inserted therein.

An introducer needle (not shown) may then be used to create the incision or puncture in the patient. The distal end of the introducer needle is advanced into the vein of the patient in the direction of flow of blood through the vein, and the proper position of the introducer needle is verified. A guidewire (not shown) may then be inserted into the vein through the introducer needle, and the needle is then removed over the guidewire. Next, if desired, a separate dilator (not shown) may be inserted over the guidewire to pre-dilate the incision prior to the introduction of the combined catheter and dilator 74. The catheter and dilator 74 combination are then inserted into the vein of the patient over the guidewire. Finally, once the catheter is properly positioned in the vein of the patient, the dilator cap member 84 of the dilator 74 is unthreaded or otherwise disconnected from the luer connector of the extension member, and the dilator 74 is removed therefrom. The catheter is then readied for conventional use by aspirating blood through the lumens and injecting normal saline and/or heparinized saline into the lumens.

FIG. 11 illustrates a modified finger member 90 on the proximal end of the wire stiffener 72 described above with respect to the prior alternate embodiment. The finger member 90 in this embodiment is preferably constructed of a preformed or bent wire or plastic member which is shaped to engage nearly any type of dilator cap member 84 on the proximal end of a dilator 74. The method of use of the stiffening wire 72 of this embodiment is the same as in the prior embodiment of the present invention as described above.

Figure 12:
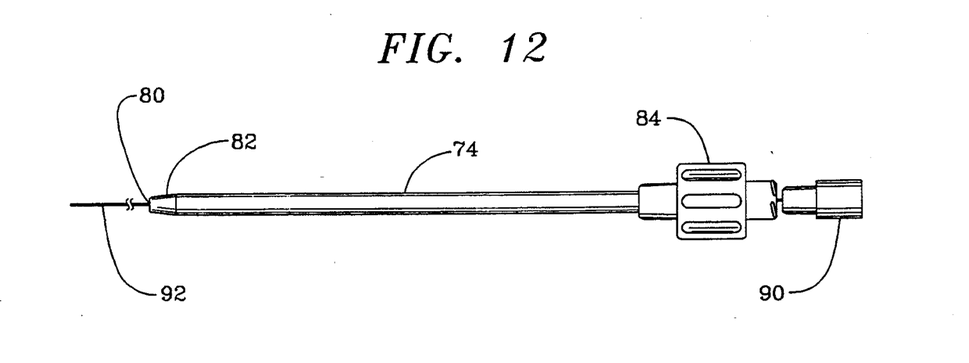
FIG. 12 is an elevated side view of an alternate embodiment of the modified dilator assembly of the type shown in FIGS. 10 and 11.

FIG. 12 also illustrates a further modification of the present invention wherein the wire of the stiffening wire 72 described above with respect to the prior embodiment functions as a pull string or flexible wire 92. The flexible wire 92 may be used with nearly any dilator 74 because it provides a relatively simple and efficient way for the user to insert the dilator 74 into a catheter. In this embodiment, the flexible wire 92 is threaded through the catheter to pull the dilator 74 into the catheter. Once the dilator 74 is properly inserted into the catheter, the flexible wire 92 is removed from the catheter and dilator 74. The dilator 74 and catheter combination are then used in the manner described above.

While the present invention is described above with respect to the preferred forms and use of the present invention, it is intended that the present invention by interpreted to encompass all modifications, equivalents and alternatives falling within the spirit and scope of the invention as defined by the appended claims.

What is claimed is:

1. A wire stiffener for use with a catheter, said wire stiffener comprising:

an elongate member having distal and proximal end portions thereon and a body portion therebetween, wherein said distal end portion includes a distal tip thereon and said proximal end includes a cap member thereon for operative connection with a catheter;

said distal tip being a generally elongate member having a first outer diameter and a passageway extending therethrough, said passageway including distally and proximally oriented openings wherein said proximally oriented opening opens generally adjacent to said body portion; and said body portion is operatively interconnected with and extends between said cap member and said distal tip and includes at least one area of increased flexibility thereon as compared to the flexibility of the remainder of said body portion.

2. The wire stiffener of claim 1 wherein said body portion includes a second outer diameter which is smaller than said first outer diameter of said distal tip.

3. The wire stiffener of claim 2 wherein said cap member includes a third outer diameter thereon and said third outer diameter is greater than said second outer diameter of said wire stiffener.

4. The wire stiffener of claim 1 wherein at least one area of increased flexibility is located further from said distal end portion than said proximal end portion along said body portion.

5. The wire stiffener of claim 1 wherein said body portion is formed of at least one elongate wire member.

6. The wire stiffener of claim 1 wherein said distal tip is a generally cylindrical member.

7. The wire stiffener of claim 1 wherein said cap member includes a luer lock type of connector thereon.

8. The wire stiffener of claim 1 wherein said cap member includes a passageway extending longitudinally therethrough.

9. The wire stiffener of claim 8 wherein said proximal portion of said elongate member includes an alignment surface thereon to capture and guide a guidewire into said passageway of said cap member.

10. A stiffener member for use with a catheter, said stiffener member comprising:

an elongate member including a proximal end portion having a cap member thereon and a distal end portion with a distal tip member thereon, and said cap member and said tip member having first and second diameters thereon;

a body portion extending between said cap member and said tip member, said body portion having a third diameter and including an area of flexibility thereon which is more flexible than the remainder of said body portion; and said cap member and said tip member further including passageways therein sized to receive a guidewire inserted therethrough wherein said passageway of said tip member includes a pair of openings therein to enable the passage of the guidewire therethrough, and said first and second diameters are greater than said third diameter.

11. A catheter assembly comprising:

an elongate wire stiffener having distal and proximal end portions thereon and wherein said proximal end portion includes a hub member thereon;

an elongate dilator having distal and proximal end portions and a lumen extending therethrough wherein said lumen is sized to receive said wire stiffener substantially therein, said proximal end portion including a hub member thereon which is formed to releasably engage said hub member of said stiffening wire; and an elongate catheter having distal and proximal end portions and at least one lumen extending therethrough wherein said lumen is sized to receive said dilator substantially therein, said proximal end portion including a hub member thereon which is formed to releasably engage said hub member of said dilator thereon.

12. The catheter assembly of claim 11 wherein said catheter is an elongate catheter having distal and proximal end portions and at least first and second lumens formed by a septum extending along a longitudinally extending axis thereof and wherein said first lumen extends between said proximal end portion and an opening on said distal end portion and is sized to receive said dilator substantially therein and said second lumen extends between said proximal end portion of said catheter and a further opening in said catheter.

13. A catheter assembly comprising:

an elongate catheter member having distal and proximal end portions and a lumen extending therebetween; and an elongate stiffening member having distal and proximal end portions with one or more wire members having a first diameter extending therebetween and an area of increased flexibility thereon as compared to the flexibility of the remainder of said stiffening member, said distal end portion forming a distal tip having a diameter which is larger than said diameter of said one or more wire members and which is sized to be received through the lumen of a catheter.

14. The catheter assembly of claim 13 wherein said distal tip includes a lumen extending therethrough and said lumen is sized to receive a guidewire therein.

15. The catheter assembly of claim 13 wherein said proximal end portion includes a hub member thereon, and said hub member includes a lumen extending therethrough, and said hub member lumen is sized to receive a guidewire therein.

16. The catheter assembly of claim 13 wherein said proximal end portion of said catheter member includes a hub member thereon, and said hub member of said catheter member is sized to receive said hub member located on said proximal end portion of said stiffener member releasably connected thereon.

* * * * *